United States Patent [19]

York, Jr.

[11] Patent Number: 4,600,717

[45] Date of Patent: * Jul. 15, 1986

[54] ALDOSE REDUCTASE INHIBITORS USEFUL IN OPHTHALMIC WOUND HEALING

[75] Inventor: Billie M. York, Jr., Fort Worth, Tex.

[73] Assignee: Alcon Laboratories, Inc., Fort Worth, Tex.

[ * ] Notice: The portion of the term of this patent subsequent to Mar. 13, 2001 has been disclaimed.

[21] Appl. No.: 599,283

[22] Filed: Apr. 11, 1984

[51] Int. Cl.$^4$ .................... A61K 31/44; A61K 31/415
[52] U.S. Cl. .................... 514/278; 514/376; 514/389; 514/409; 514/866
[58] Field of Search .................. 424/256, 273 R; 514/278, 376, 389, 409, 866

[56] References Cited

U.S. PATENT DOCUMENTS

| | | | |
|---|---|---|---|
| 3,821,383 | 6/1974 | Sestanj et al. | 424/258 |
| 4,117,230 | 9/1978 | Sarges | 548/309 |
| 4,130,714 | 12/1978 | Sarges | 548/309 |
| 4,181,728 | 1/1980 | Sarges et al. | 424/273 R |
| 4,436,745 | 3/1984 | York, Jr. | 424/273 |
| 4,438,272 | 3/1984 | York, Jr. | 548/308 |

*Primary Examiner*—Leonard Schenkman
*Attorney, Agent, or Firm*—Lowe, King, Price & Becker

[57] ABSTRACT

Method of promoting healing of ocular wounds comprising the topical application of an aldose reductase inhibitor; compositions comprising such inhibitors are also disclosed.

3 Claims, No Drawings

ALDOSE REDUCTASE INHIBITORS USEFUL IN OPHTHALMIC WOUND HEALING

BACKGROUND OF THE INVENTION

This invention relates to methods and compositions useful in promoting ocular wound healing. Specifically, this invention relates to compositions comprising an aldose reductase inhibitor; and methods of treatment comprising administering these compositions when it is desired to promote ocular wound healing.

While applicant is bound by no theory, it appears that the mechanism of wound healing is related to the mechanism of aldose reductase inhibition and the role of that event in mediating the effects of diabetes. Thus, the method and compositions of the present invention are directed to diabetic individuals. In diabetes there is a condition of high glucose or hyperglycemia. When glucose levels are high, an enzyme called aldose reductase converts glucose to sorbitol at the expense of NADPH. The accumulation of a polyol, such as sorbitol within cells causes pathological changes to those cells and in the tissues comprising those cells. These sickened cells or tissues are not capable of effecting a normal physiological response associated with wound healing (e.g., effecting normal cell migration and division). This corneal epithelium and endothelium of the eye contains aldose reductase. In diabetics the rate of cornea wound healing is retarded significantly. On occasion, vision impairing and painful corneal ulceration and scaring results from retarded or abnormal corneal wound healing in the diabetic. The aldose reductase inhibitors inhibit the enzyme aldose reductase within the cornea and thereby promote wound healing in the diabetic. These aldose reductase inhibitors can be applied topically to the eye or systemically to the diabetic to promote wound healing when indicated. While the present disclosure is premised on the above reasonings, the instant compositions and methods of the present invention are not restricted to the diabetic syndrome.

DETAILED DESCRIPTION OF THE INVENTION

Aldose reductase inhibitors which are particularly suitable for the method of the present invention and pharmaceuitcal compostions comprising these inhibitors are disclosed in the following copending, commonly assigned U.S. patent applications: U.S. patent application Ser. No. 532,168 filed Sept. 14, 1983 and U.S. patent application Ser. No. 368,630 filed Apr. 15, 1982, now U.S. Pat. No. 4,436,745; similarly, attention is directed to the following U.S. Pat. Nos.: 4,438,272; 3,821,383; 4,117,230; 4,130,714; and 4,181,728. To the extent that these applications and patents disclose aldose reductase inhibitors which are useful in the practice of the present invention, they are incorporated herein by reference.

Particularly preferred inhibitors are representatively indicated by the following list:
a. Spiro-(7-fluoro-4H-indeno[1,2-b]thiophen-4,4'-imidazolidine)-2',5'-dione;
b. Spiro-(2-fluoro-9H-fluoren-9,4'-imidazolidine)-2',5'-dione;
c. Spiro-(2-fluoro-9H-fluoren-9,3'-succinimide);
d. Spiro-(7-fluoro-5H-indeno[1,2-b]-pyridin-5,4'-imidazolidine)-2',5'-dione;
e. Spiro-(7-chloro-5H-indeno[1,2-b]-[pyridin-5,4'-imidazolidine)-2',5'-dione.
f. Spiro-(7-chloro-9H-pyrrolo[1,2-a]indol-9,4'-imidazolidine)-2',5'-dione.
g. Spiro-(2,7-difluoro-9H-fluoren-9,4'-imidazolidine)-2',5'-dione;
h. Spiro-(2,7-difluoro-9H-fluoren-9,3'-succinimide);
i. Spiro-(2,7-difluoro-9H-fluoren-9,5'-oxazolidine)-2',4'-dione.

The prefered route of administration for the compositions of the present invention is topically to the eye. The exact dosage regimen is left to the routine discretion of clinician taking into consideration the host's age, sex, weight, and his history accounting for or attributing to the ocular wound in question.

The most preferred compositions will have the chosen aldose reductase inhibitor present at a concentration ranging from 0.1% to 2.0 weight % in a vehicle selected from buffered water, aqeous buffered carbopol gel, perfluoroalkanes and/or perfluorotrialkylamines comprising a perfluoroalkane-type vehicle are fully disclosed and claimed in copending commonly assigned U.S. patent application Ser. No. 528,890 filed Sept. 2, 1983, which is incorporated herein by reference.

The following representative example illustrates suitable pharmaceutical compositions for topically delivery of the involved aldose reductase inhibitors for corneal wound healing.

EXAMPLE 1

Gel composition for topical, ocular administration:

| Ingredient | % by weight |
| --- | --- |
| 0.25% w/v of the compound Spiro-(7-chloro-5H—indeno [1,2-b]-pyridin-5,4'-imidazolidine)-2',5'-dione | 0.25% |
| Benzalkonium Chloride | 0.01% |
| Carboxypolymethylene (carbopol) | 1.0% |
| Hydrochloric Acid and/or Sodium hydroxide | to adjust pH to 5.0 to 5.5 |
| Purified Water (as gel) | q.s to 100% |

The following topical, ocular formulations are physically in the form of suspensions:

| Ingredient | % by wt. |
| --- | --- |
| Suspension A | |
| Micronized Spiro-(2-fluoro-9H—fluoren-9,4'-imidazolidine)-2',5-dione | 1.0% |
| Perfluorotributylamine (as suspension) | 99.0% |
| Suspension B | |
| Micronized spiro-(2,-7-difluoro-9H—fluoren-9,3'-succinimide) | 1.0% |
| Hydroxymethylcellulose | 1.0% |
| Disodium edetate | 0.01% |
| Benzalkonium chloride | 0.01% |
| Sodium Acetate | 0.14% |
| Sodium Chloride | 0.52% |
| Hydrochloric Acid and/or Sodium Hydroxide | pH 4.5 to 5.5 |
| Purified Water (as suspension) | q.s. to 100% |

The following formulation is a selected representative of a solution for the ophthalmic indications of the present invention:

| Ingredient | % wt. |
|---|---|
| Spiro-(2-fluoro-5H—indeno[1,2-b]pyridin-5,4'-immidazolidine)-2',5'-dione | 0.10% |
| Carboxypolymethylene (carbopol) | 0.10% |
| Benzalkonium Chloride | 0.008% |
| Hydrochloric Acid and/or Sodium Hydroxide | to adjust pH 4.5 to 5.0 |
| Purified Water | q.s. 100% |

What is claimed is:

1. A method of promoting wound healing in a wounded host organ in a diabetic host comprising topically applying to the wounded host organ a therapeutically effective, wound healing amount of a wound healing aldose reductase inhibitor, selected from the group consisting of:

a. Spiro-(7-fluoro-4H-indeno[1,2-b]thiophen-4,4'-imidazolidine)-2',5'-dione;
  b. Spiro-(2-fluoro-9H-fluoren-9,4'-imidazolidine)-2',5'-dione;
  c. Spiro-(2-fluoro-9H-fluoren-9,3'-succinimide);
  d. Spiro-(7-fluoro-5H-indeno[1,2-b]-pyridin-5,4'-imidazolidine)-2',5'-dione;
  e. Spiro-(7-chloro-5H-indeno[1,2-b]-pyridin-5,4'-imidazolidine)-2',5'-dione;
  f. Spiro-(7-chloro-9H-pyrrolo[1,2-a]indol-9,4'-imidazolidine)-2',5'-dione;
  g. Spiro-(2,7-difluoro-9H-fluoren-9,4'-imidazolidine)-2',5'-dione;
  h. Spiro-(2,7-difluoro-9H-fluoren-9,3'-succinimide) and
  i. Spiro-(2,7-difluoro-9H-fluoren-9,5'-oxazolidine)-2',4'-dione.

2. A method according to claim 1 wherein the host organ is the human eye.

3. A method according to claim 1 wherein the host is human.

* * * * *